US00PP30961P2

(12) United States Plant Patent
Buttgereit

(10) Patent No.: US PP30,961 P2
(45) Date of Patent: Oct. 22, 2019

(54) ***FUCHSIA* PLANT NAMED 'FWIPL28-0'**

(50) Latin Name: *Fuchsia hybrida*
Varietal Denomination: FWIPL28-0

(71) Applicant: Christian Buttgereit, Munster (DE)

(72) Inventor: Christian Buttgereit, Munster (DE)

(73) Assignee: Volmary GMBH (DE)

( * ) Notice: Subject to any disclaimer, the term of this patent is extended or adjusted under 35 U.S.C. 154(b) by 0 days.

(21) Appl. No.: 16/350,162

(22) Filed: Oct. 4, 2018

(51) Int. Cl.
*A01H 5/02* (2018.01)

(52) U.S. Cl.
USPC ..... Plt./300

(58) Field of Classification Search
USPC ..... Plt./300
CPC ..... A01H 5/02
See application file for complete search history.

*Primary Examiner* — Annette H Para
(74) *Attorney, Agent, or Firm* — Cassandra Bright

(57) ABSTRACT

A new and distinct *Fuchsia* cultivar named 'FWIPL28-0' is disclosed, characterized by large, purple and red-purple flowers. Plants begin flowering early in the season, flower abundantly and exhibit good garden performance. The new variety is typically produced as a garden or container plant.

2 Drawing Sheets

Figure 1:
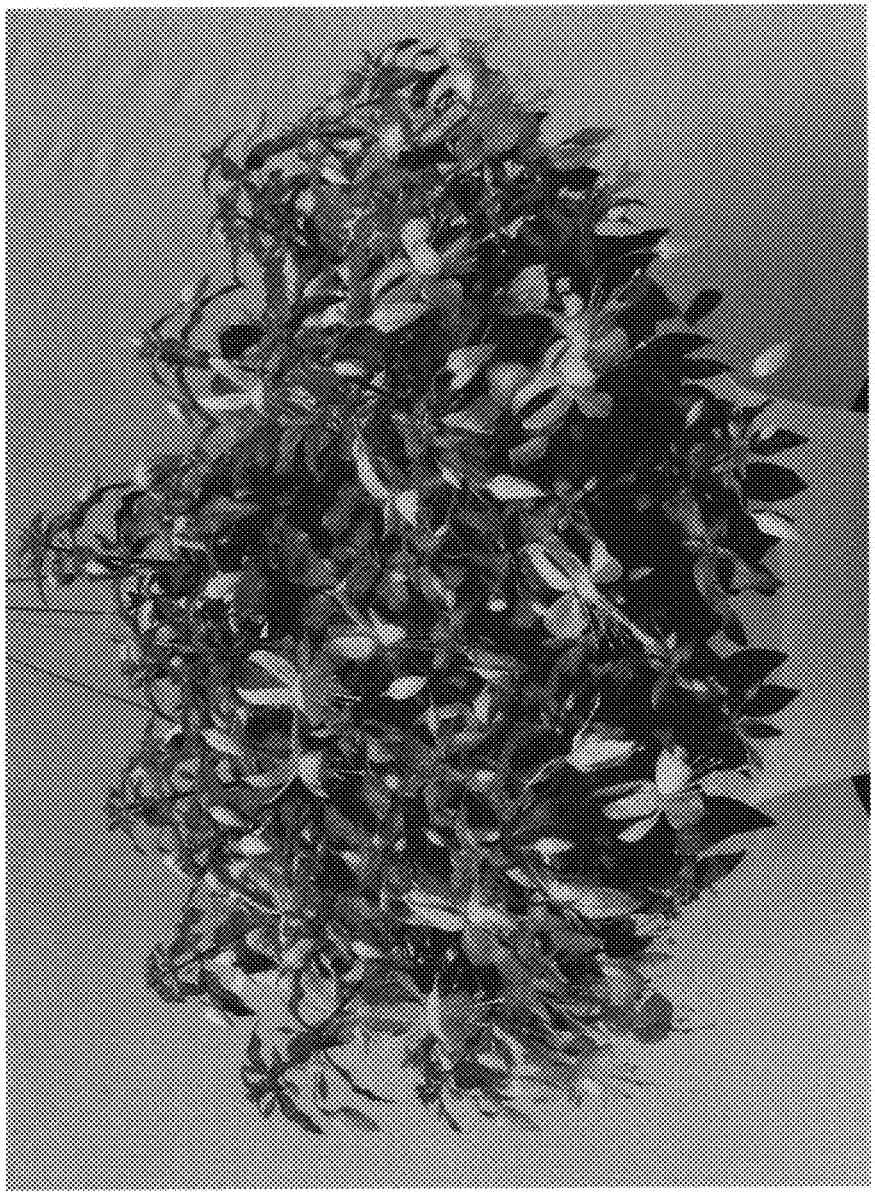

Latin name of the genus and species: *Fuchsia hybrida.*
Variety denomination: 'FWIPL28-0'.

BACKGROUND OF THE INVENTION

The new cultivar is a product of a planned breeding program. The new variety originated from a cross pollination of the seed parent, 'FUC-Z-6033' an unpatented selection of *Fuchsia* hybrid with the pollen parent, 'FUC-Z-6575', an unpatented *Fuchsia* hybrid. The crossing was made during October of 2012, at a greenhouse in Munster, Germany. 'FWIPL28-0' was discovered by the inventor, Christian Buttgereit, at the same greenhouse in 2013.

Asexual reproduction of the new cultivar 'FWIPL28-0' was first performed in Munster, Germany, by vegetative terminal cuttings during 2013. 'FWIPL28-0' has since produced three generations and has shown that the unique features of this cultivar are stable and reproduced true to type. The first sales date of this new cultivar was in February 2018.

SUMMARY OF THE INVENTION

The cultivar 'FWIPL28-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FWIPL28-0'. These characteristics in combination distinguish 'FWIPL28-0' as a new and distinct *Fuchsia* cultivar:

1. Early flowering.
2. Rich flowering over the season,
3. Large flowers.
4. Bright flower color.
5. Good garden performance.

PARENT COMPARISON

Plants of the new cultivar 'FWIPL28-0' are similar to plants of the seed parent in most horticultural characteristics, however, plants of the new cultivar 'FWIPL28-0' differ in the following:

1. 'FWIPL28-0' has an earlier flowering time than seed parent.
2. 'FWIPL28-0' has richer flowering than seed parent
3. 'FWIPL28-0' has large flowers; seed parent has medium flower size.
4. 'FWIPL28-0' has a bright flower color; seed parent has a dark flower color.
5. 'FWIPL28-0' has good garden performance; seed parent has moderate garden performance.

Plants of the new cultivar 'FWIPL28-0' are similar to plants of the pollen parent in most horticultural characteristics, however, plants of the new cultivar 'FWIPL28-0' differ in the following:

1. 'FWIPL28-0' has an earlier flowering time than pollen parent.
2. 'FWIPL28-0' has a richer flowering season than pollen parent.
3. 'FWIPL28-0' has large flowers; pollen parent has medium flower size.
4. 'FWIPL28-0' has a brighter flower color than pollen parent.
5. 'FWIPL28-0' has good garden performance; pollen parent has moderate garden performance.

COMMERCIAL COMPARISON

Plants of the new cultivar 'FWIPL28-0' are similar to plants of the unpatented commercial variety *Fuchsia* 'PB Girl' in most horticultural characteristics, however, plants of the new cultivar 'FWIPL28-0' differ in the following:

1. The new variety begins flowering earlier than comparator.
2. The new variety produces more flowers per plant than comparator.
3. The new variety produces less center petals than this comparator.
4. The new variety produces petals with more lavender/purple tones than comparator.
5. The new variety produces sepals with more lavender/purple tones than comparator.

Plants of the new cultivar 'FWIPL28-0' are also similar to plants of the unpatented commercial variety *Fuchsia* 'Jack Shahan' in most horticultural characteristics, however, plants of the new cultivar 'FWIPL28-0' differ in the following:

1. The new variety begins flowering earlier than comparator.
2. The new variety produces more flowers than comparator.
3. The new variety produces larger flowers than comparator.
4. The new variety produces sepals of a lighter color than comparator.
5. The new variety produces petals with more lavender/purple tones than comparator.

BRIEF DESCRIPTION OF THE PHOTOGRAPHS

The accompanying photograph in FIG. 1 illustrates in full color a typical plant of 'FWIPL28-0' grown outdoors in Santa Paula, Calif. This plant is approximately 20 weeks old, shown in an 10-inch pot.

Figure 2:
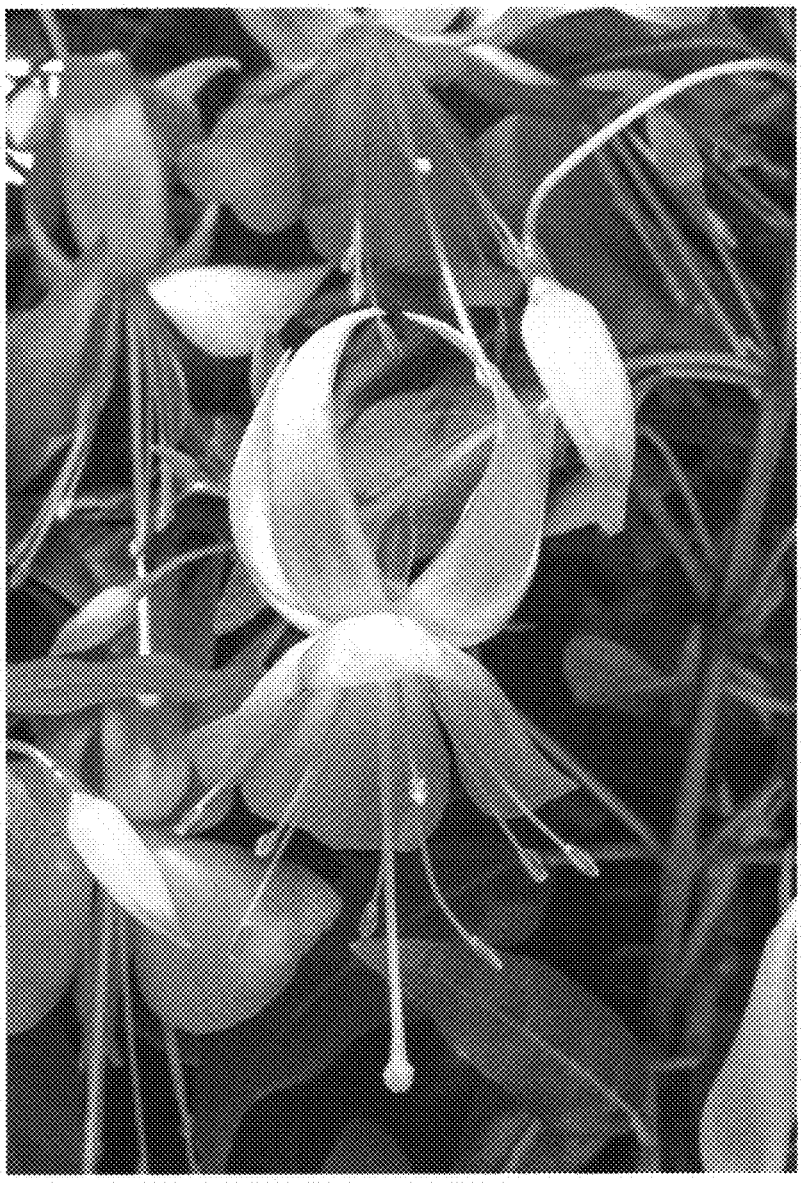

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'FWIPL28-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Fuchsia* hybrid 'FWIPL28-0'.

PROPAGATION

Propagation method: Vegetative Cuttings.

Time to initiate roots: About 2 weeks at 15° C. to 22° C.

Root description: Fine, densely fibrous. White to tan in color, not accurately measured with R.H.S. chart.

PLANT

Age of plant described: Approximately 20 weeks from 5 rooted cuttings.

Pot size of plant described: 12-inch basket.

Height: Approximately 24 cm from soil line of pot to top of foliar and uppermost flowering plane.

Plant spread: Approximately 60 cm.

Growth rate: Rapid.

Growth habit: Upright center, semi-pendulous outer branches.

Branching characteristics: Free branching.

Length of primary lateral branches: Average 18 to 28 cm.

Diameter of lateral branches: Approximately 3 to 4 cm.

Quantity of primary lateral branches: Approximately 25.

Characteristics of primary lateral branches:

*Color.*—Upper surface near Greyed-Purple N186D. Lower surfaces near Greyed-Purple N186B.

*Texture.*—Glabrous.

*Strength.*—Strong, flexible.

Internode length: Average upper internodes 2.0 cm. Lower internodes average 3.8 cm.

FOLIAGE

Leaf:

*Arrangement.*—Opposite.

*Quantity.*—Approximately 8 to 14 fully expanded leaves and 6 to 10 immature leaves per primary lateral branch.

*Average length.*—7 cm, including petiole.

*Average width.*—Average range 2.5 to 2.7 cm.

*Shape of blade.*—Ovate.

*Apex.*—Acute.

*Base.*—Rounded.

*Margin.*—Nearly entire, infrequent shallow dentations.

*Texture of top surface.*—Glabrous.

*Texture of bottom surface.*—Glabrous.

*Aspect.*—Slight overall downward curve. Slight undulation over entire leaf surface.

*Color.*—Young foliage upper side: Near RHS Green 136A. Young foliage under side: Near RHS Green 137B. Mature foliage upper side: Near RHS Green 137A. Mature foliage under side: Near RHS Green 138A.

*Venation.*—Type: Pinnate. Venation color upper side: Near RHS Yellow-Green 144C. Venation color under side: Near RHS Yellow-Green 145C. Attachment: Stalked.

*Petiole.*—Length: Average range 1.3 to 1.5 cm. Diameter: Average 2 mm. Texture: Glabrous. Color: Upper surface: Near RHS Greyed-Purple 187C. Lower surface: Near RHS Greyed-Purple 186C.

FLOWER

Natural flowering season: Spring.

Inflorescence and flower type and habit: Highly floriferous. 2 to 4 flowers emerge singly from each axil. Upper axils have 4 pairs of flowers emerging symmetrically. Flowers are symmetrical and composed of a corolla surrounded by a decorative fused calyx. Flowers face outwardly, slightly pendulous.

Flowers per plant: Approximately 200 fully open flowers and buds on a plant of this age and size.

Flower longevity on plant: Approximately 1 week for individual flowers.

Persistent or self-cleaning: Self-cleaning.

Flower size (petals and sepals only, not including protruding stamen and style):

*Length.*—Approximately 4 cm.

*Width.*—Approximately 4 cm.

Bud:

*Shape.*—Oblong.

*Length.*—2.5 cm.

*Diameter.*—9 mm.

*Color.*—Near RHS Red 56A. Veins near 58A. Some streaking near Yellow-Green 145C. Apical section near Green 142D, apex near Green 141C.

Corolla:

Petals (measured from separation at top of tube):

*Number*.—Average 4.

*Length*.—Approximately 2.0 cm.

*Width*.—Approximately 2.0 cm.

*Shape*.—Broad slightly rounded deltate.

*Aspect*.—Slightly cupped upwards or very slightly undulating.

*Margin*.—Entire.

*Texture*.—Glabrous, all surfaces.

*Appearance*.—Matte.

*Apex*.—Obtuse to truncate.

Color:

*When opening*.—Upper surface: Near RHS Purple 75C, large marginal flush 77A. Base and veins flushed Red-Purple N74B. Lower surface: Near RHS Purple 77B, margin flushed 77A. Base and veins flushed Red-Purple N74B.

*Fully opened*.—Upper surface: Near RHS Red-Purple 72A, base tinged N74C. No significant vein coloration. Lower surface: Near RHS Red-Purple 72B, base tinged N74C. No significant vein coloration.

*Fading*.—Upper surface: Near RHS Red-Purple 71B. Lower surface: Near RHS Red-Purple 71B.

Calyx:

*Form*.—Funnel form base, separating approximately 10% from base, to flare out into 4 large decorative broad elliptic shaped sepals. Sepals reflexed back with age.

*Fused section*.—Length: Approximately 5 mm. Diameter: Approximately 5 mm.

*Unfused section*.—Length: Approximately 3.0 cm. Diameter: Approximately 9 mm.

*Shape*.—Lanceolate.

*Sepal texture*.—Glabrous all surfaces.

*Appearance*.—Nearly iridescent.

*Apex*.—Acute.

*Color*.—Upper Surface: Background color near Red 56A, flushed Red 55A. Lower Surface: Background color near Red-Purple 58D, flushed 58B.

*Fragrance*.—None.

Peduncle:

*Length*.—Average range 3.0 to 5.5 cm.

*Diameter*.—1.5 mm.

*Color*.—Near RHS Yellow-Green 144B.

*Texture*.—Glabrous.

REPRODUCTIVE ORGANS

Stamens:

*Number* (*per flower*).—Typically 8.

*Filament length*.—Average 2.5 cm.

*Filament color*.—Upper section near RHS Red-Purple 68C, base near 68D.

*Anthers*.—Shape: Oblong. Length: Approximately 3 mm. Color: Near RHS Greyed-Purple 186B. Pollen: Amount: Scant. Color: Near Greyed-Orange 165B.

*Pistils*.—Quantity per flower: 1. Length: Approximately 5.5 cm. Style: Length: Approximately 5.0 cm. Color: Upper section near RHS Red-Purple N57B, mid-section near 58C, base near 69D.

*Stigma*.—Shape: Globular. Color: Near Red 51B. Ovary: Length: Approximately 5 mm. Diameter: Approximately 4 mm. Color: Near RHS Green 143B.

OTHER CHARACTERISTICS

Seeds and fruits: Fruit is an oblong berry colored near Green 143B and flushed Greyed-Purple 187B at base. Average diameter 5 to 6 mm average length 8 mm. Seed production not observed.

Disease/pest resistance: Neither resistance nor susceptibility to normal diseases and pests of *Fuchsia* has been observed.

Temperature tolerance: Tolerates temperatures from approximately −1° C. to 38° C.

Drought tolerance: No tolerance for drought.

What is claimed is:

1. A new and distinct cultivar of *Fuchsia* plant named 'FWIPL28-0' as herein illustrated and described.

* * * * *